United States Patent [19]

Yoshida

[11] Patent Number: 4,600,613
[45] Date of Patent: * Jul. 15, 1986

[54] MEDICAL BAG
[75] Inventor: Takao Yoshida, Fujinomiya, Japan
[73] Assignee: Terumo Kabushiki Kaisha, Tokyo, Japan
[ * ] Notice: The portion of the term of this patent subsequent to Dec. 5, 2001 has been disclaimed.
[21] Appl. No.: 595,335
[22] Filed: Mar. 30, 1984
[30] Foreign Application Priority Data Apr. 25, 1983 [JP] Japan .................................. 58-72398

[51] Int. Cl.⁴ ............................................. B65D 31/02
[52] U.S. Cl. ...................................... 428/35; 428/447; 604/408
[58] Field of Search ................... 428/447, 35; 604/408
[56] References Cited
U.S. PATENT DOCUMENTS 3,523,050  8/1970  Campbell .
3,849,359  11/1974  Nitzsche et al. .
4,049,873  9/1977  Creasey et al. .
4,119,267  10/1978  Kydonieus .
4,154,714  5/1979  Hockemeyer et al. .
4,337,768  7/1982  Hatada et al. .
4,490,420  12/1984  Yoshida ............................... 604/408

Primary Examiner—John E. Kittle
Assistant Examiner—Thomas C. Saitta
Attorney, Agent, or Firm—Frishauf, Holtz, Goodman & Woodward

[57] ABSTRACT

A medical bag comprising a pair of heat-sealable soft plastic sheets disposed opposing each other, said sheets having peripheral portions which are sealed together so as to form a bag main body; and substantially non-flowable, substantially continuous layers covering those portions of opposing surfaces of said sheets at least at portions of said opposing surfaces other than said peripheral portions, said substantially non-flowable layers comprising a silicone resin composition, said silicone resin composition being at least partially crosslinked.

12 Claims, 7 Drawing Figures

MEDICAL BAG

BACKGROUND OF THE INVENTION

1. Field of the Invention

The present invention relates to a medical bag and a method of manufacturing the same and, more particularly, to a soft plastic medical bag with improved blood platelet storage characteristics and improved blocking preventive characteristics, and a method of manufacturing the same.

2. Description of the Prior Art

Medical bags such as blood bags are recently made of soft plastic materials such as soft polyvinyl chloride or polyolefin-type resins. Plastic bags of this type are usually sterilized for medical safety. The sterilization of medical bags can be performed by several methods, and steam autoclaving is utilized to sterilize medical bags which contain a liquid. However, the plastic materials described above exhibit a blocking tendency at high temperatures during steam autoclaving; that is, the inner surfaces of the bag adhere to each other. Such a blocking tendency is also observed at room temperature, and the inner surfaces of the bag often adhere to each other during storage of the bag.

Further, when a blood bag is made of polyvinyl chloride, the blood platelets of the blood stored in the bag adhere to the inner surfaces of the bag, causing a poor storage performance. In order to solve this problem, it has been proposed to add to the polyvinyl chloride material a substance which imparts an anti-coagulating action to the blood platelets, and to transfer the substance onto the surface of the obtained bag. However, a satisfactory result has not been obtained.

SUMMARY OF THE INVENTION

It is an object of the present invention to provide a medical bag which is made of a soft plastic material and which prevents adhesion of blood platelets thereto, and a method of manufacturing the same.

It is another object of the present invention to provide a medical bag which prevents blocking, and a method of manufacturing the same.

According to the present invention, there is provided a medical bag comprising:

a pair of heat-sealable soft plastic sheets which are placed opposing each other and are sealed together at their peripheries to constitute a bag main body; and substantially non-flowable, substantially continuous layers which entirely cover those portions of the opposing surfaces of said sheets at least other than the heat-sealing portions thereof, and which comprise a silicone resin composition, said silicone resin composition being at least partially crosslinked.

In general, the non-flowable layers have gel-like surfaces, and the silicone resin composition preferably contains dimethylsiloxane units as a main component.

The resin composition preferably further contains aminoalkylsiloxane units which are at least partially crosslinked with the dimethylsiloxane units. In this case, the resin composition preferably contains about 80 to 95% by weight of dimethylsiloxane units and about 20 to 15% by weight of aminoalkylsiloxane units.

The aminoalkylsiloxane units can be derived from an aminosilane coupling agent. Such an aminosilane coupling agent can be selected from the group consisting of γ-(2-aminoethyl)aminopropyltrimethoxysilane, γ-(2-aminoethyl)aminopropylmethyldimethoxysilane, and mixtures thereof.

The non-flowable layers are preferably formed in an amount of about $5 \times 10^{-4}$ to $1.5 \times 10^{-2}$ g/m$^2$ on each opposing surface of the sheets.

The sheets themselves normally exhibit a blocking tendency.

In a preferred aspect of the present invention, each sheet consists of soft polyvinyl chloride.

In a medical bag of the present invention, the non-flowable layers can be non-continuously formed at the sealed portions of the sheets such that the sheets are adhered together directly at the non-continuous portions of the non-flowable layers.

A medical bag of the present invention as described above can be manufactured by preparing a pair of heat-sealable soft plastic sheets; coating a 0.05 to 1.5% by weight solution of a silicone resin composition on one substantially entire surface of each of said sheets, which silicone resin composition has at least partial crosslinkability; at least partially crosslinking the silicone resin composition so as to form substantially non-flowable, substantially continuous layers each of which covers the one substantially entire surface of each of said sheets; and heat-sealing those portions of said sheets which correspond to the above-noted sealing portions so as to constitute a bag with said pair of sheets superposed such that said non-flowable layers oppose each other.

The heat-sealing described above is preferably performed by high-frequency induction heating if the plastic material used (e.g., polyvinyl chloride) can be sealed by such heat-sealing.

The term "main component" used in the specification and the claims indicates that the corresponding component (e.g., dimethylsiloxane units) is contained in an amount exceeding 50% of the total weight of the resin composition. The reference to "crosslinking of dimethylsiloxane" herein means not only crosslinking between dimethylsiloxane units but also crosslinking of dimethylsiloxane units with aminoalkylsiloxane units mentioned above. The term "blocking" indicates a phenomenon wherein the material of the bag sticks or adheres together at room temperature or at high temperatures such as during steam autoclaving. Plastic materials generally exhibit such a blocking tendency.

DETAILED DESCRIPTION OF THE PREFERRED EMBODIMENTS

Figure 1A:
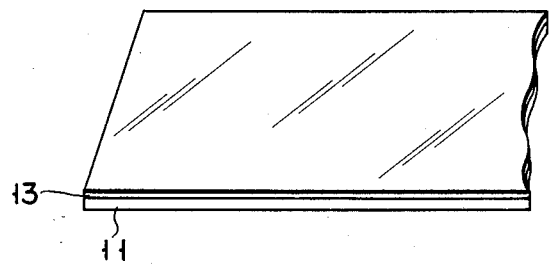
FIGS. 1A to 4 are views for explaining in sequential order a method of manufacturing a medical bag according to the present invention.

In order to prevent adhesion of blood platelets and blocking in a medical bag manufactured from a soft plastic material, the present inventor studied the modification of plastic surfaces, which would not impair the heat-sealability of the plastic and would not interfere with steam autoclaving.

As a result of such studies, it was found that the adhesion of blood platelets to a bag can be most effectively suppressed by polydimethylsiloxane. However, polydimethylsiloxane has a liquid form and cannot be fixed directly on a plastic surface, in particular, a polyvinyl chloride surface. Plasma treatment of a plastic surface can be performed so as to fix polydimethylsiloxane on the plastic surface. However, although plasma treatment of a plastic surface can indeed allow fixing of polydimethylsiloxane thereon, such plasma-treated plastic surfaces cannot be heat-sealed to a standard such that they may not be separated upon subsequent steam autoclaving. Plasma-treated plastic surfaces may appear to be properly sealed upon heat-sealing, but when these plastic surfaces are subsequently autoclaved, they are frequently separated. It was also found that a film of polydimethylsiloxane cannot withstand autoclaving.

According to further studies made by the present inventors, the following fact was also determined. When a silicone resin composition containing dimethylsiloxane units as a main component is coated on a plastic surface and the dimethylsiloxane units are at least partially crosslinked, the dimethylsiloxane can be fixed on the plastic sheet without having its ability to prevent adhesion of blood platelets impaired, and can be satisfactorily heat-sealed such that it can withstand autoclaving without experiencing separation. When such a silicone resin composition is used, blocking of the plastic sheets is prevented. When the plastic sheet consists of soft polyvinyl chloride, elution of a plasticizer usually contained therein can be prevented.

The silicone resin composition to be used herein preferably contains dimethylsiloxane units as a main component; that is, it contains dimethylsiloxane units in an amount exceeding 50% by weight of the total weight of the resin composition. The balance of the silicone resin composition comprises a crosslinking component with the dimethylsiloxane units. Therefore, the silicone resin composition is at least partially crosslinkable, and upon being crosslinked forms a non-flowable layer. Since it is preferable that the dimethylsiloxane units in the silicone resin composition are not completely crosslinked, the crosslinking component is preferably contained in an amount exceeding 5% by weight. The preferable silicone resin composition provides a gel-like surface upon being crosslinked, and the cross-linked portions are present on the surfaces of the sheets.

A preferable example of the crosslinking component is other siloxane units which can be crosslinked with dimethylsiloxane.

An example of an at least partially crosslinkable silicone resin composition to be used herein contains aminoalkylsiloxane-dimethylsiloxane units and is described in, for example, the specification of Japanese Patent Publication No. 46-3627. An example of such a composition comprises a copolymer consisting of 5 to 20% by weight of aminoalkylsiloxane units and 95 to 80% by weight of dimethylsiloxane units. When such a copolymeric composition is coated on a plastic surface, it reacts at room temperature with atmospheric moisture and is crosslinked. A composition of this type is commercially available in a solution form as "MDX-4-4159" from Dow-Corning Corp. Alternatively, the crosslinking component can be derived from a silane coupling agent. The silane coupling agent is crosslinked with the dimethylsiloxane units and provides a non-flowable layer in a similar manner, according to the present invention. Examples of such a silane coupling agent include an aminoalkylsilane such as γ-(2-aminoethyl)aminopropyltrimethoxysilane (e.g., "Toray SH6020"), γ-(2-aminoethyl)aminopropylmethyldimethoxysilane (e.g., "Toray SH6023"), or a special aminosilane mixture available as "Toray SH6026" from TORAY INDUSTRIES, INC.; methyltrimethoxysilane (e.g., "Toray SZ 6070"); or a mercaptoalkylsilane such as γ-mercaptopropyltrimethoxysilane (e.g., "Toray SZ 6062"). An aminoalkylsilane and a mixture thereof are particularly preferable. When a silane coupling agent selected from those enumerated above is mixed in the amount described above in polydimethylsiloxane, a silicone resin composition to be used herein can be provided. This latter silicone resin composition also reacts at room temperature with atmospheric moisture and is crosslinked.

According to the present invention, the silicone resin composition as described above is coated on two opposing surfaces of a pair of sheets of a bag so as to prevent both the adhesion of blood platelets to the bag and blocking. Therefore, the silicone resin composition and hence the non-flowable layers to be formed upon crosslinking such a composition need not be formed on the entire opposing surfaces of the sheets and need be coated only on those portions of the sheet surfaces which define the interior of the bag. However, from the point of view of ease in manufacture, it is convenient to coat the silicone resin composition on the entirety of each of the opposing surfaces of the sheets, as will be described later with reference to the drawings. This is because coating of the silicone resin composition on only those portions of the sheet surfaces which define the interior of the bag is rather cumbersome.

The coated amount of the silicone resin composition after drying is preferably $5 \times 10^{-4}$ g/m$^2$ or more. When the coated amount of the silicone resin composition is less than this, the ability to prevent adhesion of blood platelets and blocking is impaired. Although the upper limit of the coated amount of the silicone resin composition is not particularly limited, it is preferably $1.5 \times 10^{-2}$ g/m$^2$ when the composition is coated on the entire surface of each sheet. When the coated amount exceeds this amount, it becomes somewhat difficult to heat-seal the plastic sheets through the non-flowable layers formed upon crosslinking of the silicone resin composition.

The silicone resin composition is generally coated in the form of a solution. From the viewpoint of preventing adhesion of blood platelets, the contentration of the silicone resin composition solution must be 0.05% by weight or more, and is preferably 1.5% by weight or more. When the sheets are to be adhered through the non-flowable layers formed upon crosslinking of the silicone resin composition, the upper limit of the concentration of the silicone resin composition solution is 1.5% by weight, preferably 1.0% by weight. The solvent can be Freon or the like.

A preferred embodiment of a method of manufacturing a medical bag according to the present invention will now be described with reference to the accompanying drawings.

Figure 1B:
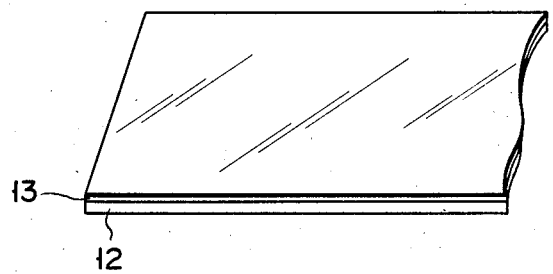

In order to manufacture a medical bag according to the present invention, a pair of elongated sheets 11 and 12 of a heat-sealable thermoplastic plastic material (e.g., polyvinyl chloride, polyolefin such as polyethylene, an ethylene-vinyl acetate copolymer or the like) which exhibits a blocking tendency at high temperatures in, for example, steam autoclaving (in superheated saturated steam at 110° C. to 130° C.), are used, as shown in FIGS. 1A and 1B. As shown in these figures, the silicone resin composition solution layer 13 is formed continuously on an entire major surface of each sheet 11 or 12 with a brush or the like.

Figure 2:
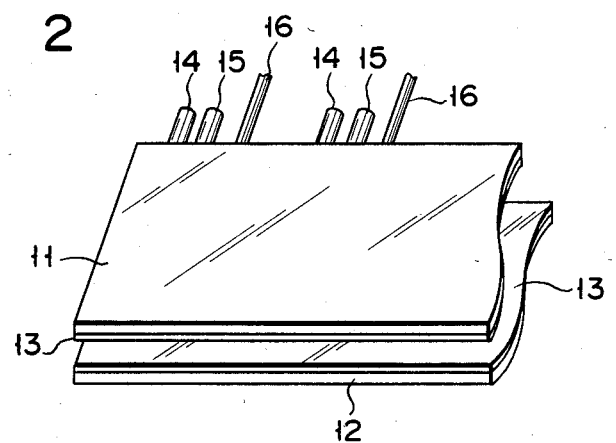

The silicone resin composition solution layer 13 formed on each sheet 11 or 12 is dried at room temperature (e.g., for 15 minutes). Thereafter, as shown in FIG. 2, the sheets 11 and 12 are superposed upon each other such that the layers 13 oppose each other. When a blood bag, for example, is to be manufactured, predetermined outlet ports 14 and 15 and a transfusion tube 16 are inserted between the sheets 11 and 12 at predetermined intervals therebetween in a direction perpendicular to the longitudinal direction of the sheets 11 and 12. The predetermined portions of the sheets which correspond to the periphery of each bag obtainable therefrom is subsequently heat-sealed.

Figure 3A:
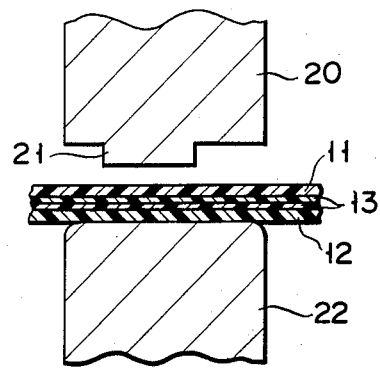

Since the non-flowable layers 13 are formed on the entire inner surfaces of the sheets 11 and 12, the predetermined portions of the sheets are heat-sealed by being pressed and heated by press molds. In this case, the shapes of the molds are not particularly limited. However, as shown in a sectional view in FIG. 3A, an upper mold 20 preferably has a projection 21 having a surface corresponding to the bag periphery, and a lower mold 40 (support mold) 22 preferably has a relatively wide flat surface.

Figure 3B:
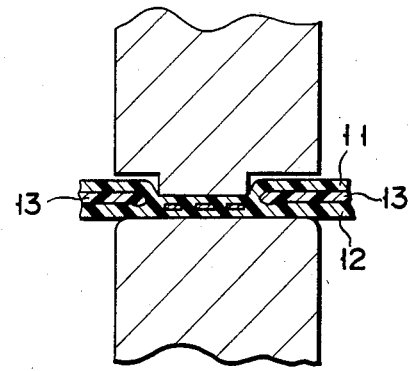
Figure 4:
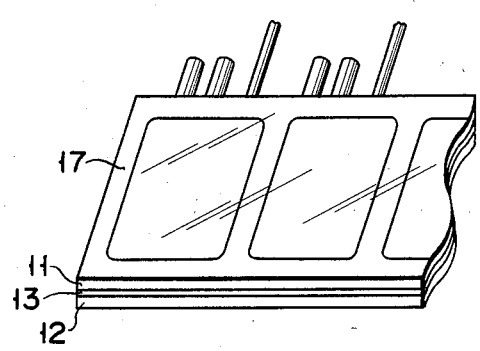
Figure 5:
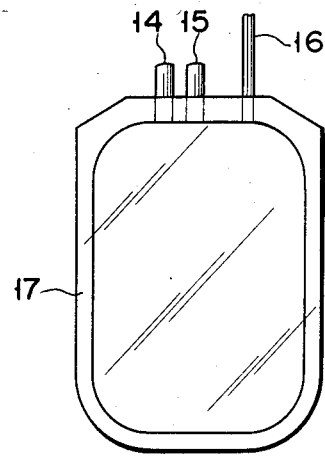
FIG. 5 is a plan view of the medical bag of the present invention.

In the manner shown in FIG. 3B, the predetermined portions of the sheets is pressed and heat-sealed with the molds 20 and 22. Upon heating, the sheet material is partially melted and flows to the sides causing breaks in the layers 13. Then, the sheets 11 and 12 are adhered together through such break portions in the layers 13. The heat-sealing temperature is above the melting temperature of the sheets 11 and 12. In this manner, despite the presence of the layers 13 between the sheets 11 and 12, the sheets 11 and 12 can be securely adhered together and will not be separated upon autoclaving. FIG. 4 shows the sheets 11 and 12 which are heat-sealed in this manner (the heat-sealed portions are designated by reference numeral 17). Heat-sealing is preferably performed by high-frequency induction heating when the plastic sheets consist of a material having a high-frequency wave sealability, such as polyvinyl chloride or an ethylene-vinyl acetate copolymer. The sheets 11 and 12 of the structure shown in FIG. 4 are cut along the heat-sealed portion which is formed along the longitudinal direction of the bag. Then, the bag 5 as shown in FIG. 5 is obtained. The bag can be sterilized by autoclaving (e.g., in superheated saturated steam at 110° C. to 130° C. for 15 to 45 minutes).

The present invention will now be described by way of its example.

EXAMPLE

A pair of sheets consisting of soft polyvinyl chloride containing dioctyl phthalate (DOP) as a plasticizer were prepared. A commercially available silicone resin (Dow-Corning "MDX-4-4159") containing 50% resinous constituents of aminoalkylsiloxane and dimethylsiloxane was diluted in Freon to prepare a 0.5% resin solution. The resin solution was then coated on one surface of each sheet, and was cooled naturally to crosslink and cure the resin.

The sheets were then superposed upon each other such that the silicone resin layers opposed each other. The periphery of the sheets were then heat-sealed by high-frequency induction heating to prepare a blood collection bag.

The characteristics of the bag thus prepared were compared with those of a bag which was prepared without being coated with the silicone resin. The obtained results are shown in Table 1 below.

TABLE 1

|  | The Invention | | | Control | | |
|---|---|---|---|---|---|---|
| DOP elution amount (in plasma)* | 178 μg/ml | | | 367 μg/ml | | |
| DOP elution amount (in concentrated red blood cells)* | 85 μg/ml | | | 116.2 μg/ml | | |
| Blood platelet adhesion** | Type I 23.4% | Type II 51.0% | Type III 25.6% | Type I 11.4% | Type II 48.6% | Type III 40.0% |
| High-frequency sealing strength | 4.5 kg/cm | | | 4.7 kg/cm | | |
| Blocking tendency*** | 230 g/2 cm (width) | | | 598 g/2 cm (width) | | |

Notes:
*Measurements were made after leaving the plasma or concentrated red blood cells to stand for 24 hours after sampling.
**Measurements were made following the procedure of the blood platelet elongation test described in the section 3 "Blood Tests" of Rinshokensa Gijutsu Zensho (A Treatise on Clinical Testing Technique) (1972), P. 478. Types I, II, and III were classified according to the section entitled "The reaction of blood platelet on surfaces of polymeric materials for medical purposes" in "Jinko-Zoki" (Artificial Organs), 9(1), pp. 228 to 231 (1981).
***Measurements were made after leaving samples in an autoclave at 121° C. for 30 minutes.

No elution of the silicone resin into plasma or concentrated red blood cells was observed.

The medical bag of the present invention consists of a pair of sheets of a resin which normally exhibits a blocking tendency at high temperatures during steam autoclaving. However, since layers of at least partially crosslinked reactive silicone resin are formed on the inner surfaces of the bag, the inner surfaces of the bag may not in fact adhere to each other upon autoclaving.

Since the silicone resin layers prevent adhesion or elongation of the blood platelets, the storage characteristics of the platelets are improved when the medical bag of the present invention is used as a blood bag. Particularly if the sheets are made of soft polyvinyl chloride, the silicone resin serves to prevent elution of the plasticizer, providing an excellent blood bag.

The silicone resin may not elute into the infusion solution or into blood, thus providing a safe medical bag.

The silicone resin layers are formed in a gel-like form on the surface of each sheet. Therefore, although the silicone resin layers are present at the heat-sealed portion, heat-sealing can be performed without any problem. This allows easy coating of the sheets with a silicone resin solution. Since the silicone resin layers are non-flowable, handling of the bag is easy.

What is claimed is:

1. A medical bag comprising:

a pair of heat-sealabe soft plastic sheets disposed opposing each other, said sheets having peripheral portions which are sealed together so as to form a bag main body; and substantially non-flowable, substantially continuous layers covering those portions of opposing surfaces of said sheets at least at portions of said opposing surfaces other than said peripheral portions, said substantially non-flowable layers comprising a silicone resin composition, said silicone resin composition being at least partially crosslinked.

2. A medical bag according to claim 1, wherein said silicone resin composition contains dimethylsiloxane units as a main component.

3. A medical bag according to claim 2, wherein said substantially non-flowable layers have gel-like surfaces.

4. A medical bag according to claim 3, wherein the crosslinked portion of the silicon resin composition is present in said substantially non-flowable layers and on the surfaces of the sheets.

5. A medical bag according to claim 2, wherein the resin composition further contains aminoalkylsiloxane units which are at least partially crosslinked with the dimethylsiloxane units.

6. A medical bag according to claim 5, wherein the resin composition contains about 80 to 95% by weight of dimethylsiloxane units and about 20 to 15% by weight of aminoalkylsiloxane units.

7. A medical bag according to claim 5, wherein the aminoalkylsiloxane units are derived from an aminosilane coupling agent.

8. A medical bag according to claim 7, wherein the aminosilane coupling agent is a member selected from the group consisting of γ-(2-aminoethyl)aminopropyltrimethoxysilane, γ-(2-aminoethyl)aminopropylmethyldimethoxysilane, and mixtures thereof.

9. A medical bag according to claim 2, wherein said substantially non-flowable layers are formed in an amount of about $5 \times 10^{-4}$ to $1.5 \times 10^{-2}$ g/m² on the entire one surface of each of said sheets.

10. A medical bag according to claim 2, wherein said sheets have a blocking tendency.

11. A medical bag according to claim 10, wherein said sheets consist essentially of soft polyvinyl chloride.

12. A medical bag according to claim 2, wherein said substantially non-flowable layers form non-continuous portions at said heat-sealed peripheral portions of said sheets and said sheets are adhered together through said non-continuous portions of said substantially non-flowable layers.

* * * * *

UNITED STATES PATENT AND TRADEMARK OFFICE
CERTIFICATE OF CORRECTION

PATENT NO. : 4,600,613

DATED : July 15, 1986

INVENTOR(S) : Takao YOSHIDA

It is certified that error appears in the above-identified patent and that said Letters Patent is hereby corrected as shown below:

On the Title Page, left column, next to the heading designated "Notice:" change "Dec. 5, 2001" to --Dec. 25, 2001--.

Signed and Sealed this

Sixteenth Day of December, 1986

*Attest:*

DONALD J. QUIGG

*Attesting Officer*  *Commissioner of Patents and Trademarks*